US009629378B2

(12) United States Patent
Harting Glade et al.

(10) Patent No.: US 9,629,378 B2
(45) Date of Patent: Apr. 25, 2017

(54) DISPERSION OF PHYTOSTEROLS

(76) Inventors: Thomas Francis Harting Glade, Las Condes (CL); Miguel Angel Fuenzalida Diaz, Las Condes (CL); Alejandro Markovits Rojas, Las Condes (CL)

( * ) Notice: Subject to any disclaimer, the term of this patent is extended or adjusted under 35 U.S.C. 154(b) by 308 days.

(21) Appl. No.: 13/202,862

(22) PCT Filed: Jan. 29, 2010

(86) PCT No.: PCT/IB2010/050414
§ 371 (c)(1),
(2), (4) Date: Oct. 31, 2011

(87) PCT Pub. No.: WO2010/095067
PCT Pub. Date: Aug. 26, 2010

(65) Prior Publication Data
US 2012/0046254 A1 Feb. 23, 2012

(30) Foreign Application Priority Data

Feb. 23, 2009 (CL) ..................................... 409-2009

(51) Int. Cl.
| A61K 31/575 | (2006.01) |
| A61P 3/06 | (2006.01) |
| A23D 7/005 | (2006.01) |
| A23C 9/13 | (2006.01) |
| A23C 9/152 | (2006.01) |
| A23L 27/60 | (2016.01) |
| A23L 33/11 | (2016.01) |

(52) U.S. Cl.
CPC .............. *A23D 7/0056* (2013.01); *A23C 9/13* (2013.01); *A23C 9/152* (2013.01); *A23D 7/0053* (2013.01); *A23L 27/60* (2016.08); *A23L 33/11* (2016.08); *A23C 2240/10* (2013.01)

(58) Field of Classification Search
None
See application file for complete search history.

(56) References Cited

U.S. PATENT DOCUMENTS

| 6,063,776 | A | 5/2000 | Ostlund | |
| 6,190,720 | B1 * | 2/2001 | Yuan et al. ................... | 426/601 |
| 6,423,363 | B1 * | 7/2002 | Traska et al. ................. | 426/604 |
| 6,677,327 | B1 * | 1/2004 | Gottemoller ................. | 514/182 |
| 2001/0006672 | A1 | 7/2001 | Akashe et al. | |
| 2002/0064548 | A1 | 5/2002 | Yoon et al. | |
| 2003/0165572 | A1 * | 9/2003 | Auriou ........................ | 424/493 |
| 2004/0014733 | A1 | 1/2004 | Binder et al. | |
| 2004/0029844 | A1 * | 2/2004 | Yoon ..................... | A23C 9/152 |
| | | | | 514/169 |
| 2005/0170064 | A1 | 8/2005 | Yoon et al. | |
| 2006/0035009 | A1 | 2/2006 | Gaonkar et al. | |
| 2007/0031570 | A1 * | 2/2007 | Binder et al. ................. | 426/604 |
| 2007/0141224 | A1 * | 6/2007 | Zawistowski .......... | A23D 7/001 |
| | | | | 426/611 |
| 2009/0004359 | A1 | 1/2009 | Orikoshi et al. | |

FOREIGN PATENT DOCUMENTS

WO WO 02065859 A1 * 8/2002
WO WO 2006/046686    5/2006

OTHER PUBLICATIONS

Gabriel D. Fernandes, Rosana M. Alberici, Gustavo G. Pereira, Elaine C. Cabral, Marcos N. Eberlin, Daniel Barrera-Arellano. Direct characterization of commercial lecithins by easy ambient sonic-spray ionization mass spectrometry. Food Chemistry 135 (2012) 1855-1860.*
V. Jenning, A. Lippacher and S. H. Gohla. Medium scale production of solid lipid nanoparticles (SLN) by high pressure homogenization. J. Microencapsulation, 2002, vol. 19, No. 1, 1±10.*
Martin Mittelbach. "Lipase Catalyzed Alcoholysis of Sunflower Oil", JAOCS, vol. 67, No. 3 (Mar. 1990), pp. 168-170.*
Supplementary European Search Report and Written Opinion for EP 20100743456 (mailed Feb. 20, 2015).

* cited by examiner

*Primary Examiner* — Frederick Krass
*Assistant Examiner* — Michael P Cohen
(74) *Attorney, Agent, or Firm* — Merchant & Gould P.C.

(57) ABSTRACT

The invention relates to a method for the production of highly stable aqueous dispersions of phytosterols, phytostanols and derivatives thereof, which allows the use of a wide range of emulsifiers in relatively small concentrations in relation to the phytosterols and which allows the preparation of dispersions with high concentrations of phytosterols. Said dispersions are obtained using a method in which one or more phytosterols, an aqueous medium and one or more emulsifiers are dispersed in a disperser at a temperature of at least 140° C. in order to obtain an emulsion and the resulting emulsion is subsequently cooled in order to obtain a dispersion of sterols in an aqueous medium.

9 Claims, No Drawings

DISPERSION OF PHYTOSTEROLS

This application is a National Stage Application of PCT/IB2010/050414, filed 29 Jan. 2010, which claims benefit of Serial No. 409-2009, filed 23 Feb. 2009 in Chile and which applications are incorporated herein by reference. To the extent appropriate, a claim of priority is made to each of the above disclosed applications.

FIELD OF THE INVENTION

The present invention relates to a process for producing highly stable aqueous dispersions of phytosterols and the utilization of these dispersions as ingredients of hypocholesterolemic food and pharmaceutical products.

BACKGROUND OF THE INVENTION

Sterols in general, mainly plant sterols or phytosterols, currently have numerous applications and are most commonly used as food ingredients. Such applications require the use of phytosterols dispersed in aqueous media such as dairy beverages, aqueous fancy drinks, fruit juices, or in lipidic media like margarines and mayonnaise among others. Since the applications of dispersed phytosterols are so numerous, it is important to have highly stable aqueous dispersions that can be stored for long periods before being used in diverse applications and simultaneously provide homogeneous products when used in specific applications, wherein phytosterols remain dispersed, no phase separation takes place and the products have good palatability. The interest of the food industry for the elaboration of phytosterol-containing products is a result of the proven capacity of phytosterols to inhibit the absorption of dietary cholesterol.

Since the 1930's, it has been known that plasmatic cholesterol levels are affected by the ingestion of phytosterols. Later research conducted around the 1950's has definitively shown, both in animals and humans, that phytosterols are very efficient at inhibiting the absorption of externally provided cholesterol, i.e. dietary cholesterol. Consequently, people ingesting phytosterols with their cholesterol-containing food have a lower level of serum cholesterol than those whose food does not contain phytosterols. As a result, there has lately been a great interest on the elaboration of phytosterols-containing food products as an effective and low-cost way to provide phytosterols for those in need thereof.

Although phytosterols are not soluble in aqueous media and are hardly soluble in fatty media, phytosterols have not to be soluble in the ingested food to exert their hypocholesterolemic effect, but are capable of exhibiting their cholesterol-lowering effect when dispersed in these media. Although the cholesterol-lowering effect of phytosterols is well known in the state of the art, it has been surprisingly found that phytosterol dispersions prepared according to the process of the present invention have a significantly higher cholesterol-lowering effect than similar dispersions prepared according to processes known in the state of the art and have higher cholesterol-lowering effects achieved using one of the most known commercial products having this effect, namely phytostanol esters.

Usually, in the preparation of aqueous dispersions of phytosterols, one or more surface active agents are used as emulsifiers which are added to the preparation in a proportion over 20% by weight in relation to phytosterols, which is typically over 50%. Most of the water-dispersible phytosterol powders contain about 50% phytosterols that consists of one part phytosterols and one part emulsifiers or other additives. Although dispersible phytosterol powders containing up to 85% by weight of phytosterols can be found in the market, said powders have a very poor dispersibility in water, and once suspended in water at 1% by weight they separate from the aqueous phase easily and settle down in less than one hour. In order to stabilize such dispersions, they require higher amounts of emulsifiers and further processing, usually by high-pressure homogenization, which implies additional more complicated formulation steps. Currently, there are no commercially available stable aqueous dispersions of phytosterols that could be used as functional food ingredients, mainly because they settle down easily, have a low phytosterol content in the dispersion (high water content) and have a limited shelf life (less than one month). Therefore, dispersions are usually dehydrated and commercialized as resuspendable powders. In the following sections, the terms surface-active agent and surfactant are used interchangeably.

Food emulsifiers constitute only a relatively small group of the emulsifier family, and many of them have dietary restrictions concerning their daily intake, which in some cases such as polysorbates can be as low as 25 mg/kg. This limits the combination of emulsifiers that can be used in the phytosterol dispersion processes. This problem is more serious when more than one surfactant must be used in the dispersion, when they have to be incorporated in food or pharmaceutical products.

The suggested daily intake of phytosterols as cholesterol-lowering agents is between 0.8 and 2.0 g, therefore, in case that they are accompanied by high levels of food emulsifiers, the total daily intake of food emulsifiers considering emulsifiers present in other food items as well might very well surpass the maximum allowable daily intake for some emulsifiers or in the case of mono- or diglycerides they might significantly increase the overall daily calorie intake.

There is a need, therefore, to develop solutions to obtain highly stable aqueous phytosterol dispersions with the lowest possible emulsifier/phytosterol ratio, using the whole range of food emulsifiers, including predominantly hydrophobic and predominantly hydrophilic surfactants or their mixtures.

There are a large number of processes disclosed in the prior art aimed at the preparation of aqueous phytosterol suspensions or dispersions and their use as an ingredient of hypocholesterolemic food. Some of the most relevant prior art documents of the past 20 years concerning the subject matter disclosed in the present application are shown in Table 1.

In the present invention the term emulsion has the usual meaning, that is, an emulsion is a mixture of two immiscible liquids wherein one of the liquids, known as the dispersed phase, is dispersed within the other liquid, known as the continuous phase. Therefore, an aqueous phytosterol emulsion means a dispersion of liquid phytosterols in an aqueous medium, while the term aqueous dispersion of phytosterols refers to the dispersion of solid phytosterols in an aqueous medium. To form a stable emulsion, the emulsion should contain one or more surface-active agents and sometimes also other components known generically as protective colloids. Surface-active agents or surfactants are substances that have both hydrophilic and hydrophobic portions in the same molecule, i.e. they have an amphiphilic character. This means that they have the tendency to concentrate in the interface, so reducing the interfacial tension. To characterize the degree of amphiphilicity of an amphiphilic molecule, an empirical numerical scale ranging from 1 to 40, denominated the HLB value, is used. The lower the HLB value, the more hydrophobic the molecule is and, conversely, the higher the HLB value, the higher is the hydrophilic character of the molecule. There are a large number of surface-active agents, both natural and synthetic, which are useful for a variety of applications. An emulsifying agent is a surface-active agent utilized in the preparation of emulsions with the aim of stabilizing the emulsion. It has been found empirically that those surface-active-agents having HLB number ranging from 8 to 18 are useful for stabilizing oil in water emulsions (o/w) wherein the disperse phase is oil and the continuous phase is water or an aqueous medium. On the other hand, surface-active agents which have an HLB number ranging from 3 to 6 are useful for stabilizing water in oil emulsions (w/o), wherein the disperse phase is water and the continuous phase is oil. In the field of emulsions, the term oil means any liquid that is immiscible with water. The term aqueous medium means either water or a solution, dispersion or w/o emulsion containing at least 30% of water by weight of solution, dispersion or emulsion.

There are numerous disclosures in the state of the art concerning the preparation of dispersible phytosterols in aqueous media comprising mechanical dispersion of phytosterols in aqueous media in the presence of one or more surface-active agents, the dissolution of phytosterols in some suitable solvent, either sub- or super-critical followed by the dispersion of the dissolution in an aqueous phase, the preparation of water-soluble phytosterol complexes, the thermal dissolution of phytosterols in one or more surface-active agents followed by the dispersion of the dissolution in an aqueous media, the direct mixing of phytosterols with an aqueous solution of some surface-active agent followed by the injection of live steam at high temperature and many others.

With the exception of the process disclosed in the US Patent Appl. 20060035009 in which phytosterols are solubilized by preparing a water-soluble phytosterol-carbohydrate complex, the general approach for obtaining phytosterol preparations has been either by preparing water-

TABLE 1

State of the art processes for the preparation of phytosterol dispersions.

| Document number | Inventor | Title |
| --- | --- | --- |
| EP1645267A2 | Behnam, Dariush | Method for producing an active ingredient concentrate and active ingredient concentrate. |
| 20070031570 | Binder, Thomas P. | Hydrothermically processed compositions containing phytosterols. |
| 6623780 | Stevens, Luke Alan | Aqueous dispersible sterol products. |
| 20070141224 | Zawistowski, Jerzy | Compositions comprising one to more phytosterols and/or phytostanols, or derivatives thereof, and high HLB emulsifiers. |
| 20060035009 | Gaonkar, Anilkumar | Compositions and processes for water-dispersible phytosterols and phytostanols. |
| WO/2002/065859 | Auriou, Nicolas | Stabilized dispersions of phytosterol in oil. |
| 20030165572 | Auriou, Nicolas | Water-dispersible encapsulated sterols. |
| 20050170064 | Yoon, Won-tae | Plant sterol-containing food, and method for preparing the same. |
| WO/2003/077680 | Yoon, Won-tae | Mixing powder of plant sterol and emulsifier, and method for preparing the same. |
| 20070231447 | Fleckenstein, Michael | Sterol compositions and methods of making the same. |
| EP1575378A1 | Auweter, Helmut | Pulverulent phytosterol formulations. |
| 6316030 | Kropf, Christian | Use of nanoscale sterols and sterol esters. |
| 20040033202 | Cooper, Eugene R. | Nanoparticulate sterol formulations and novel sterol combinations. |
| WO/1999/063841 | Stewart, David John | Compositions comprising phytosterol and 7 or phytostanol having enhanced solubility and dispersibility. |
| 20050244488 | Spilburg, Curtis A. | Methods and formulations for enhancing the absorption and gastrointestinal bioavailability of hydrophobic drugs. |
| 6110502 | Burruano, Brid | Method for producing water-dispersible sterol formulations. |
| WO/2002/017892 | Auriou, Nicolas | Stabilized dispersions of phytosterol in oil. |
| 7306819 | Lerchenfeld, Erich | Beverages containing plant sterols. |
| 7335389 | Lerchenfeld, Erich | Beverages containing plant sterols. |
| 20070014819 | Wu, Wen-teng | Method of emulsifying phytosterol by natural saponin, emulsion prepared thereby and water-dispersible phytosterol powder product. |
| 20040142087 | Lerchenfeld, Erich P | Beverages containing plant sterols. |
| WO/2003/103633 | Cooper, Eugene R | Nanoparticulate sterol formulations and sterol combinations. |
| WO/2003/094891 | Spilburg, Curtis A. | Methods and formulations for enhancing the absorption and gastro-intestinal bioavailability of hydrophobic drugs. |
| 20020064548 | Yoon, Won-tae | Methods for dispersing plant sterol in aqueous phase and plant sterol-dispersed beverages. |
| WO/2003/000075 | Dyer, Matthew | Method for manufacturing of free-flowing powder containing water-dispersible sterols. |
| WO/2001/053320 | Stewart, David John | Crystalline composites comprising phytosterols and phytostanols or derivatives thereof. |
| WO/2007/124597 | Stewart, David John | Compositions comprising one or more esterified phytosterols and/or phytostanols into which are solubilized on or more unesterified phytosterols and/or phytostanols, in order to achieve therapeutic and formulation benefits |
| 6113972 | Corliss, Glenn | Phytosterol-protein complexes. |
| WO/2006/074752 | Veldhuizen, Yvonne | Sachets comprising plant sterol. |
| 20030003131 | Dyer, Matthew | Method for manufacture of free-flowing powder containing water-dispersible sterols. | dispersible phytosterol powders or aqueous phytosterol dispersions to get hypocholesterolemic effects. Ostlund, in the U.S. Pat. Nos. 5,932,562 and 6,063,776, also discloses processes for obtaining water-soluble phytosterols, but as shown in the Example 4 of the '562 patent, powdered sitostanol preparations did not exhibit cholesterol-lowering effects in human subjects. With the exception of the three documents above, the state of the art discloses a variety of methods either for the preparation of water-dispersible phytosterol powders or aqueous phytosterol dispersions, which in general are more readily obtained than water-soluble phytosterols. But as shown by Ostlund in the '562 patent, the efficacy of phytosterol powders or dispersions as cholesterol-lowering agents seems to depend on their preparation process.

When comparing the cholesterol-lowering effect of aqueous dispersions of phytosterols or water-dispersible phytosterol powders prepared according to the present invention with those prepared according to processes known in the state of the art, a significantly higher cholesterol-lowering effect has been observed in the first case, which would confirm that the cholesterol-lowering effect of solid phytosterols ingested as water-dispersible powders or aqueous phytosterol dispersions seem to depend, though unpredictably, on the process of their preparation.

There are numerous well-known methods for the dispersion of immiscible liquid phases to prepare emulsions. The preferred methods utilized in the present invention are those that resort to rotor/stator homogenizers such as colloid mills, stirred vessels and pressure homogenizers. This equipment is capable of providing high shear stress and shear rate allowing the preparation of aqueous phytosterol emulsions that give rise to aqueous phytosterol suspensions upon cooling with characteristics that are surprisingly different from the dispersions prepared using any of the processes of the state of the art.

The processes of the state of the art do not disclose any phytosterol dispersion process wherein phytosterols, an aqueous medium and one or more food-grade surface-active agents, with a low surface-active agent to phytosterols ratio and having significant phytosterol concentrations for use in the food or pharmaceutical industry, are dispersed at temperatures above the melting point of phytosterols to form an emulsion, followed by cooling down said emulsion to originate a phytosterol dispersion in aqueous medium.

On the contrary, this procedure has been discouraged in the documents of the state of the art considering the high melting point of phytosterols. In fact, in the U.S. Pat. No. 6,623,780 (Sep. 23, 2003) entitled "Aqueous dispersible sterol product", the inventors (Stevens and Schmeltzer) explicitly state (see column 3, line 10 and following) that "The primary difficulty in formulating sterols is their high melting point. Commercially available food-grade sterols typically have a melting point range of 120° C.-140° C. This makes their dispersion in water very difficult because the sterols cannot be dispersed in water as liquid sterols without resorting to high temperatures and associated high pressures."

In order to overcome what they considered a difficulty, the inventors resorted to mixing sterols, monoglycerides and a polysorbate such as Tween 60. This gives rise to a mixture with a lower melting point, which is around 75° C. The mixture is then cooled down, preferably by spraying the mixture into an air stream. The resulting sterol-emulsifier powder can subsequently be dispersed in an aqueous medium and be subjected to high-shear homogenization to form an emulsion, i.e. the incorporation of sterols into food matrixes requires the use of subsequent homogenization steps. According to the type and proportions of the claimed surface-active agents, the HLB value of the surface-active agent mixture ranges from 4 to 6 and the claimed ratio of emulsifiers to sterols ranges from 111% to 170%. The inventors have found that a dispersion prepared according to their invention, containing sterols, monoglycerides and polysorbates, is stable in pure water for several weeks.

By contrast, aqueous phytosterol dispersions prepared in accordance with the processes of the present invention have a shelf life of more than one year without any noticeable phase separation or settling during said period and are easily incorporated into liquid food items such as dairy beverages, aqueous fancy drinks, fruit juices and the like.

One of the disadvantages of the process disclosed in U.S. Pat. No. '780 is that in order to prepare a more or less stable aqueous phytosterol dispersion several steps are required i.e. mixing the sterols with one or more emulsifying agent, melting the mixture formed, spray-drying the melted product, and dispersing the resulting powder in an aqueous medium under high shear at a temperature higher than the melting point of the powder. Besides, in order to get a significant melting point reduction of the mixture of sterols and emulsifiers, a similar or higher amount of emulsifiers is required relative to the sterols utilized. In addition, a shelf life of a few weeks could be insufficient for certain applications. Furthermore, the range of usable emulsifiers is rather restricted in the disclosed process, leaving numerous important food emulsifiers out of the application field. Additionally, the large excesses of emulsifiers that accompany the sterols might contribute significantly to the calorie content of the food articles in which they are incorporated, an undesirable feature for cholesterol-lowering foods.

Yoon et al. in the US Patent Applications 20040029844, 20040170064 and 20020064548 disclose a similar process for the preparation of aqueous phytosterols, resorting to lower ratios of emulsifier/phytosterol that those used by Stevens and Schmeltzer in U.S. Pat. No. '780 but at the expense of using higher temperatures, closer to the melting point of sterols, which was precisely the problem that the inventors of the U.S. Pat. No. 6,623,780 wanted to avoid.

In the above quoted patent applications, the disclosed processes consist in mixing sterols with several emulsifiers at temperatures between 130° C. and 140° C. as illustrated in the Examples 1, 2 and 3 of the Patent Application 20040029844, in order to form a melted mixture. This mixture can be dispersed in an aqueous medium or drink, preferably between 70° C. and 90° C. The process is carried out in a mixer-stirrer with a rotation speed of 6,800 rpm to 10,000 rpm. The inventors state that, "after the stirring process, a homogenizing process is needed to pulverize aggregated micelles".

The emulsifiers used were sucrose stearyl ester, sorbitan lauryl ester, sodium stearyl lactylate, polyglycerine monostearate and monoglyceryl citrate, in amounts varying from 17% to 85%, relative to sterols. The range of HLB values of these emulsifiers ranges from 8 to 15.

As shown in the Comparative Examples 1, 2 and 3 of the Patent Application 20040029844, when the emulsifiers used were sodium stearyl lactylate, polysorbate or monoglyceryl citrate, the resulting dispersions were unstable. According to the Examples, only sucrose stearyl ester (HLB 11) and lauryl sorbitan (HLB 8.6) and their mixtures were effective stabilizers. Therefore, the range of emulsifiers suitable for carrying out the disclosed invention is rather limited. According to the Examples of the present invention, the sterol dispersion prepared according to the Example 1 of the Application 20040029844 without the homogenization step (assay 5) is unstable, and when the homogenization step is included (assay 6), the resulting dispersion has considerably less stability than the sterol dispersion prepared according to the present invention. In addition, the process disclosed in the Application 20040029844 does not allow for the preparation of aqueous phytosterol dispersions with high solid contents.

Binder, in the US Patent Application 20070031570, discloses a method for the preparation of aqueous phytosterol dispersions by mixing water, phytosterols and an emulsifier and then heating the mixture with live steam between 100° C. and 200° C. for a period ranging from 2 seconds to 10 minutes, preferably from 30 seconds to 3 minutes. The heating process exerts a characteristically low shear stress upon the mixture. Then, the mixture is either cooled down in flash cooler or is further homogenized at a high pressure ranging from 2000 psi to 8000 psi, preferably twice. The specification does not disclose the homogenization temperature, but in the Example 1, after a hydrothermal process at 152° C., the mixture is cooled down to 79° C. and subjected to a two-stage homogenization step. Hence, the real homogenization is carried out on an aqueous dispersion of solid sterols.

To carry out the disclosed process, food-grade emulsifiers with low HLB values (lower than 5), such as lecithins, distilled mono and diglycerides and the like, are used. The amount of emulsifiers relative to the phytosterols in the Examples 1 and 2 was 199%.

Among the disadvantages of the disclosed process the following can be set forth: the range of emulsifiers utilizable is rather limited to emulsifiers with HLB values less than 5, which leaves out important emulsifiers required in certain applications; the product before the homogenization step is very unstable, and even after this homogenization step the product still has low stability; in addition, the product uses large excesses of emulsifiers in relation to the amount of phytosterols, which might be disadvantageous for its application in cholesterol-lowering foods which are usually required to be low-calorie foods as well.

Another disadvantage of the disclosed process, common to other processes in the state of the art, is inherent to the homogenizing step of aqueous dispersion of solid sterols due to the serious abrasion caused to the homogenizer valves. In the process of the present invention, homogenization is carried out over sterol emulsions, not dispersions. The consequence of this is not only the expected lack of abrasion, but also, unexpectedly, the resulting dispersion turns out to have surprising characteristics, such as a higher stability, the possibility of using a large range of emulsifiers at very low concentrations relative to the phytosterols and in the presence of large phytosterol concentrations.

It is evident that there is no process in the state of the art to prepare aqueous phytosterol suspensions having a very high stability, stabilized by one or more surface-active agents selected from a wide array of emulsifiers comprising both hydrophilic and hydrophobic emulsifiers with HLB values ranging from about 1 to about 20, that allows the production of dispersions with a low phytosterol content and also dispersions with more than 10%, preferably more than 20% phytosterols based on the weight of the aqueous dispersion.

The process disclosed in the present invention allows the preparation of highly stable phytosterol dispersions using a wide array of food-grade emulsifiers and their mixtures, with HLB numbers between 1 and 20, with low emulsifier/phytosterol ratio, and is an extremely simple process that can be satisfactorily carried out in a single step. The concentration range of phytosterols in the dispersions of the present invention ranges from 0.1 g to 400 g of phytosterols dispersed per liter of dispersion, which are two orders of magnitude higher than the highest concentrations achieved for any stable phytosterol dispersion disclosed in the state of the art. This is another advantage of the process of the invention, since aqueous dispersions with high phytosterol content are preferable in certain applications wherein high concentration of dispersed phytosterols are required, such as e.g. in margarine additives. Likewise, when the aim is obtaining a dispersible powder, it is preferable to begin with a dispersion that has the lowest water content possible in order to reduce the difficulties related to water removal.

Although the present invention was motivated by the detected necessity of providing a process to obtain phytosterol dispersions wherein the product of the process could overcome all the disadvantages of the phytosterol dispersions obtained using the processes disclosed in the state of the art, it has been found that dispersions prepared according to the process herein disclosed, both aqueous dispersions as well as resuspended powdered phytosterols, unexpectedly and surprisingly exhibited a significantly higher cholesterol-lowering effect with respect to the effect exhibited by dispersions of the state of the art, as will be shown in Example 16.

BRIEF DESCRIPTION OF THE INVENTION

To prepare highly stable aqueous phytosterol dispersions, phytosterols, an aqueous medium and one or more emulsifiers are mixed and dispersed in a suitable disperser at a temperature above the melting point of the phytosterols to obtain an aqueous phytosterol emulsion, followed by cooling down the emulsion to yield a highly stable aqueous phytosterol dispersion. The process invented and described in detail in what follows allows for the preparation of aqueous phytosterol dispersions having a surprisingly high stability, with an average particle size of less than 1000 nm even at high phytosterol concentration based on the weight of the final dispersion. Suitable dispersers to carry out the invention include rotor-stator dispersers such as colloidal mills, stirred vessels with flat blade turbine stirrers, Cowles impellers, pointed blade impellers, saw-tooth impellers and many other mixer-stirrer designs, such as mixing equipment from Silverson Machines and pressure homogenizers.

DETAILED DESCRIPTION OF THE INVENTION

The first objective of the present invention is to provide a process for the preparation of highly stable aqueous phytosterol dispersions to be used as food or pharmaceutical ingredients or formulated in diverse applications.

The second objective of the present invention is to provide a process for the preparation of highly stable aqueous phytosterol suspensions to be used either alone or as a food or pharmaceutical ingredient for the reduction of the absorption of dietary cholesterol in human subjects at levels significantly higher than those exhibited by similar phytosterol-containing products of the state of the art. To prepare dispersions with such characteristics, a phytosterol or a mixture of phytosterols, an aqueous medium and one or more emulsifiers are mixed and dispersed in a suitable disperser at a temperature above the melting point of the phytosterols to obtain an aqueous phytosterol emulsion, followed by cooling down the emulsion to yield a highly stable aqueous phytosterol dispersion. Suitable dispersers to carry out the first step of the present invention include rotor-stator dispersers such as colloidal mills, stirred tanks with flat blade turbine stirrers, Cowles impellers, pointed blade impellers, saw-tooth impellers and many other mixer-stirrer designs, such as Silverson Machines mixers and pressure homogenizers.

The third objective of the present invention is to provide a process for the preparation of powdered water-dispersible phytosterols to be used either alone or in the preparation of a food or pharmaceutical product to be administered to human subjects to inhibit the absorption of dietary cholesterol at levels significantly higher than those exhibited by similar products containing powdered phytosterols of the state of the art. For the preparation of powdered phytosterols with such characteristics, a phytosterol or a mixture of phytosterols, an aqueous medium and one or more emulsifiers are mixed and dispersed in a suitable disperser at a temperature above the melting point of the phytosterols to obtain an aqueous phytosterol emulsion, followed by cooling down the emulsion to yield a highly stable aqueous phytosterol dispersion. Suitable dispersers to carry out the first step of the present invention include rotor-stator dispersers such as colloidal mills, stirred tanks with flat blade turbine stirrers, Cowles impellers, pointed blade impellers, saw-tooth impellers and many other mixer-stirrer designs, such as Silverson Machines mixers and pressure homogenizers. The dispersions obtained are subsequently dehydrated in order to get water-dispersible powdered phytosterols.

A convenient technique for the measurement of the stability of an aqueous phytosterol dispersion, used in the present invention and in the disclosures of Stevens and Schmeltzer and Yoon et al., is the quantification of the amount of phytosterols separating from a dispersion upon centrifuging the dispersion under standardized conditions. To this end, an amount of dispersion having a certain phytosterol concentration is centrifuged at 3000 g for 10 minutes and the resulting phytosterol concentration in the supernatant is measured. The stability of the original dispersion is expressed in terms of the yield of phytosterols that remain in suspension after the centrifugation. The less the amount of separated phytosterols, the higher the stability of the dispersion (see Equation 1):

$$E = M1 * X1 / (M0 * X0) * 100, \quad \text{(Equation 1)}$$

wherein:
E: Stability of the dispersion, %
M0: Mass of centrifuged dispersion, g
X0: Percentage of phytosterols in the centrifuged dispersion, %
M1: Mass of recovered dispersion, g
X1: Percentage of phytosterol in the recovered dispersion, %

Under the assay conditions, in the phytosterol dispersions prepared according to the process disclosed in the present invention, no phytosterol precipitation is observed or the stability of the dispersion is higher than 75% after the centrifugation. That is, over 75% of the sample phytosterols remain in suspension after the centrifugation assay.

In the present invention the term "phytosterol" includes free sterols of plant origin such as sitosterol, campesterol, stigmasterol, brassicasterol, avenasterol or mixtures of said specific free plant sterols, as well as the hydrogenated form of these free sterols known as phytostanols, such as sitostanol, campestanol and their mixtures, and also phytosterol o phytostanol esters with organic acids, such as fatty acids, succinic acid, ferulic acid and other acids, mixtures of said esters and generally esters with acids having from 1 to 24 carbon atoms, glycosides and other derivatives thereof.

Mixtures of phytosterols or specific phytosterols can be obtained from a variety of oleaginous seeds such as soybean, corn, sunflower, cotton, raps and the like. They can also be obtained from by-products of the paper pulping industry, such as tall oil soaps, tall oil, or the residue of the distillation of tall oil, known as tall oil pitch.

The surface-active agents or emulsifiers useful for the present invention comprise a wide variety of surface-active agents or emulsifiers, especially food-grade surface-active agents or emulsifiers having HLB values ranging from 1 to 20, some of which are illustrated in Table 2.

TABLE 2

| Food emulsifiers | |
|---|---|
| Emulsifier | HLB number |
| Monoglycerides | 3-4 |
| Diglycerides | 2-6 |
| Acetic acid esters of monoglycerides | 1 |
| Lactic acid esters of monoglycerides | 3-4 |
| Citric acid esters of monoglycerides | 9 |
| Succinic acid esters of monoglycerides | 5-7 |
| Diacyl tartaric acid esters of monoglycerides | 8-10 |
| Polyglycerol esters of fatty acids | 4-14 |
| Sorbitan esters of fatty acids | 2-9 |
| Polyoxyethylene sorbitan esters of fatty acids | 10-17 |
| Polypropylene glycol esters of fatty acids | 1-3 |
| Sucrose esters of fatty acids | 1-16 |
| Calcium or sodium stearyl lactylate | 7-9 |
| Lecithin | 3-4 |
| Sodium or potassium salts of fatty acids | 14-20 |

The first objective of the present invention can be achieved by mixing phytosterols, one or more food emulsifiers, preferably food-grade emulsifiers, having HLB numbers ranging from 1 to 20, and an aqueous medium, preferably water, most preferably soft water. In the case that only hard or semi-hard water is available, this can be softened by means of techniques well known in the state of the art, including chemical treatments, ion exchange or distillation. Once dispersions are prepared according to the processes of the present invention, said dispersions can be mixed with a wide array of products to be used in food, drinks, nutraceuticals, pharmaceutical or cosmetic products.

Besides water, other aqueous media that can be used to prepare phytosterol dispersions in the present invention are natural aqueous solutions, emulsions or dispersions used preferably in the food industry, such as milk, whey and whey products, juices and their derivatives, solutions and bases for preparing fantasy drinks, aqueous derivatives of soy and other seeds, herbal infusions, alcoholic drinks, and the like.

For each gram of phytosterols in the dispersion, the amount of emulsifier might range from 100 μg to 1000 mg, preferably the amount will be within the range from 10 mg to 200 mg. The amount of phytosterols in the dispersion might range from 100 mg to 500 g per liter of dispersion. In the state of the art the highest phytosterol content disclosed in a phytosterol dispersion is less than 200 g/liter.

The selection of the type and amount of emulsifier or mixture of emulsifiers to be used will depend on the specific requirements of the users. Specific formulations are described in the examples to illustrate the invention, but they do not limit the scope of the invention, which allows a person skilled in the art to perform other specific applications tailored to specific requirements without affecting the stability of the phytosterol dispersion in the particular formulation.

An additional advantage of the processes disclosed in the present invention is their capability to make dispersions with high phytosterol content, since in certain applications, such as creams, specialty margarines or in cases when the desired end products are dispersible phytosterol powders, it might be advantageous or even necessary to utilize very concentrated emulsions or dispersions.

Subsequently, the mixture is heated to a temperature between 140° C. and 250° C., preferably between 150° C. and 200° C., resulting in a liquid mixture formed by the phytosterols, emulsifiers and the aqueous medium, and the liquid mixture is then dispersed in a suitable disperser to form an aqueous emulsion of phytosterols. The heating and dispersing of the mixture can be done in closed stirred vessels provided with a heat transfer system such as coiled coils or a jacket, where a suitable heat transfer fluid circulates at a desired temperature, or the heating can be carried out using a heating bath at a desired temperature wherein the vessel is partially or totally immersed.

It is convenient to carry out the phytosterol emulsification process in the absence of oxygen to reduce the risk of oxidation of either the phytosterols or the emulsifiers, due to the high temperatures attained during the emulsification process. This can be done, for example, by performing the emulsification process in a closed stirred vessel wherein the head volume is filled by nitrogen gas. The mixture of phytosterols, aqueous medium and emulsifier or emulsifiers is fed into the reactor displacing part of the nitrogen in the vessel, excepting what remains in the head space of the reactor.

Another convenient way to eliminate oxygen from the stirred vessel is first evacuating the air from the vessel by means of a vacuum pump and then feeding the mixture of phytosterols, aqueous medium and emulsifier or emulsifiers into the reactor before heating such mixture.

The mixture of phytosterols, aqueous medium and emulsifier or emulsifiers is heated in the closed vessel up to the desired temperature, typically between 140° and 200° C., with stirring. Once the desired temperature is reached stirring is maintained for a period ranging from 1 second to 1 hour, after which the heating is stopped and the mixture is cooled down, usually under 140° C. The cooling down of the emulsified mixture can be carried out either by natural convection, stopping the heating and letting the mixture to cool down by itself, or by forced convection, circulating a cold fluid inside the jacket or the coil and keeping the stirring rate. Once the emulsified mixture is cooled down, a highly stable aqueous phytosterol dispersion is obtained, with an average particle size usually smaller than 1000 nm.

The emulsification of the mixture of phytosterols, aqueous medium and one or more emulsifiers can also be conveniently carried out in dispersers consisting in on-line mixers and bottom-fed mixers. The emulsification process can be carried out in a continuous process in any of the aforementioned mixers. When the emulsification process is carried out in a continuous process, the removal of air can be done, for example, by first heating the aqueous medium up to between 90° C. and 95° C. then passing it to a deareator, such as a packed column, and then feeding the deareated aqueous medium, phytosterol and one or more emulsifiers into the continuous mixer. The emulsion leaving the continuous mixer is then cooled down to obtain a highly stable aqueous phytosterol dispersion, having an average phytosterol particle size smaller than 1000 nm.

When the emulser used in a batch or in a continuous process, either alone or in combination with other emulsifiers, is a salt of an organic acid in a proportion of at least 0.5% by weight with respect to the phytosterols, the resulting dispersion is surprisingly translucent, with an average particle size smaller than 100 nm. Salts which lead to such dispersions include the sodium or potassium salt of organic acids having from 1 to 24 carbon atoms, preferably from 10 to 24 carbon atoms. These organic acids can be saturated, mono or poly-unsaturated organic acids. The salts can be added directly to the mixture to be dispersed or can be formed in situ during the emulsification process by means of the neutralization of the corresponding organic acid with sodium or potassium hydroxide that is incorporated into the emulsified mixture. As shown in the Examples, the present invention allows the surprising formation of highly stable aqueous phytosterol dispersions, with an average particle size of about 100 nm, using no more than 1% of emulsifiers relative to the phytosterol content.

The dispersion processes of the present invention can be carried as well, if desired, in the presence of one or more protective colloids, such as gelatin, chitosan, casein, Arabic gum, starches, and polymers such as polyvinyl alcohols, polyvinyl pyrrolidones, and polyalkylene glycols, among many others. Preferably, said protective colloids can be directly mixed into the dispersion, into the emulsion or into the mixture of phytosterols, one or more emulsifiers and the aqueous medium. The use of a protective colloid is particularly convenient when the dispersion or the subsequent application of the dispersion will endure very large storage periods.

The abovementioned dispersion processes can be carried out as well, if desired, in the presence of an ant caking agent comprising starches (high amylose starch, corn starch, octenyl succinylated starch, acetylated starch), dextrins (maltodextrin, cyclodextrins, isodextrins), proteins (wheat gluten, wheat flour, wheat flour concentrate, soy meal, soy meal concentrate) and crystal growth inhibitors (polyglycerol esters, polyglycerol polyricinoleates). Preferably, the anti-caking agent can be directly mixed into the dispersion, into the emulsion or into the mixture of sterols, one or more emulsifiers and aqueous medium. The use of an anti-caking agent is especially advantageous when the final product is dispersible phytosterol powder.

If desired, it is also possible to obtain an aqueous phytosterol dispersion with a much smaller average size and with less size dispersion around the average size, if instead of cooling down the aqueous emulsion formed, said emulsion is further homogenized either in a homogenizer or in a colloidal mill. If a homogenizer is used, the emulsion of phytosterols is fed into a homogenizer operating at a pressure from 30 to 3000 bars and at a temperature from 140° C. to 250° C., preferably from 150° C. to 200° C. If desired, the mixture can be homogenized in a single-stage or multiple-stage homogenizer, preferably in a two-stage homogenizer. If the homogenization is carried out in two stages, the pressure in the first stage can range from 100 to 3000 bars, while the pressure in the second stage can range from 25 to 100 bars. The emulsion leaving the homogenizer yields a highly stable aqueous dispersion of phytosterols when cooled down.

An additional advantage of the process of the present invention with respect to the processes of the state of the art is the use of high temperature homogenization with no presence of solid particles in the homogenized mixture. Phytosterol dispersions are actually homogenized in the current state of the art processes. At high pressures such as those at which homogenization processes operate, the presence of solid phytosterol particles can exert a considerable abrasive effect on the homogenizer valves, which is not observed using the process of the present invention.

Alternatively, the preparation of stable aqueous dispersions of phytosterols can be also carried out by feeding into a one-stage or two-stage homogenizer a mixture of phytosterols, an aqueous medium and one or more emulsifiers, wherein the mixture fed into the homogenizer at a temperature ranging from 140° C. to 250° C., preferably from 150° C. to 200° C. In the case that the homogenization is carried out in a two-stage homogenizer, the pressure in the first stage can range from 30 to 2000 bars and in the second stage from 20 to 100 bars. The emulsion discharged from the homogenizer, yields a stable aqueous dispersion of phytosterols when cooled down.

For certain applications, the use of dispersible phytosterol powders that can be readily resuspendable in an aqueous medium to yield a dispersion is desirable.

To obtain such dispersible phytosterol powders, the emulsified or dispersed mixture obtained by any of the previously disclosed processes, comprising an aqueous medium, phytosterols, one or more emulsifier and optionally one or more anti-caking agent, can be further dehydrated preferably by spray-drying the emulsion in a spray-dryer with a rotary disc or nozzle atomizers at a temperature between 80° C. and 250° C. The operation can be carried our either in a co-current or a counter-current process. The resulting dispersible phytosterol powder has an average particle size larger than 1 micron, which is relatively large, comparable to those obtained in processes of the state of the art. However, despite such a relatively large particle size, the dispersible phytosterol powder obtained using the processes disclosed in the present invention exhibited a surprisingly high cholesterol-reducing effect.

Therefore, the first objective of the present invention is obtained by means of a process comprising:
  a) dispersing one or more phytosterols, an aqueous medium and one or more emulsifiers in a disperser, at a temperature of at least 140° C., to obtain an emulsion; and
  b) cooling down the emulsion to obtain an aqueous dispersion of phytosterols.

To achieve the second objective of the invention food or pharmaceutical compositions comprising a phytosterol dispersion prepared according to the disclosed processes, or directly any of the dispersions obtained using any of the disclosed processes, are administered to human subjects. The phytosterol dispersions of the present invention can be suitably incorporated into a variety of food products, food supplements, food additives, nutraceuticals and beverages such as dairy products (cheese, butter, milk, ice cream, yoghurt and the like), fatty foods (margarine, mayonnaise, lard, edible oils and the like), cereal-based products (bread, biscuits, pasta, doughs and the like), candies and confectionery products (chocolates, caramels, chewing gum and the like), alcoholic and non-alcoholic beverages (including soft drinks, juices, dietary supplements and the like), miscellaneous products (eggs and egg-derived products, processed food, pre-mixes, prepared sauces, powdered soups and the like), dietary supplements (beverages, cereal bars, tablets, capsules and the like) or sachets for direct use. The phytosterol dispersions of the present invention can be suitably incorporated into a variety of pharmaceutical and cosmetic preparations, including capsules, soft capsules, syrups, solutions, ointments, creams or gels, together with suitable excipients and/or diluents, stabilizers or active compounds. These preparations comprise from 10 mg to 50 g of phytosterols contained in the dispersion for each 100 g of the formulated product.

To inhibit the absorption of dietary cholesterol in human subjects in a degree significantly higher than the reduction observed when the same subjects are administered phytosterol-containing products prepared according to the state of the art techniques, human subjects are administered periodically, typically on a daily basis, a food or pharmaceutical composition or a phytosterol dispersion with a total amount of phytosterols ranging from 0.1 g to 3.0 g per day.

To achieve the third objective of the present invention, phytosterol powders or food and pharmaceutical compositions comprising phytosterol powders obtained according to the processes disclosed in the present invention are administered to human subjects. According to the present invention, phytosterol powders can be suitably incorporated into food items such as milk beverages, soft drinks, alcoholic beverages, fruit juices, yoghurt, ice cream, mayonnaise, margarine, cereal based products such as bread, pasta, biscuits, doughs, powdered soups, powdered milk, sauces and others. Pharmaceutical forms suitable for the incorporation of phytosterol powders comprise pharmaceutical syrups, capsules and pills. The food or pharmaceutical compositions comprise from 10 mg to 50 g of phytosterol powder per 100 g of formulated product.

In the present invention, to inhibit the absorption of dietary cholesterol in human subjects in a degree significantly higher than the reduction observed when the same subjects are administered phytosterol powders prepared according to the state of the art techniques, the human subjects are administered periodically, typically on a daily basis, a food or product comprising an amount of phytosterols from 0.1 g to 3.0 g per day.

EXAMPLES

In the following examples, unless stated otherwise, tall oil phytosterols corresponding to the composition shown in Table 3 were used. Throughout the examples, soft water and food-grade emulsifiers were utilized.

TABLE 3

| Tall oil phytosterol composition. | |
|---|---|
| Phytosterol | % in weight |
| Campesterol | 7.0 |
| Campestanol | 1.4 |
| Stigmasterol | 0.8 |
| Sitosterol | 75.3 |
| Sitostanol | 12.0 |
| Other phytosterols | 3.3 |

In order to compare the stability of phytosterol dispersions prepared according to the processes disclosed in the present invention with those phytosterols dispersions prepared according to processes of the state of the art on the same basis, phytosterol dispersions were prepared as disclosed in the assay No. 5 of the Example 1 of the US Patent Application 20040029844 and in the Example 1 of the US Patent Application 20070031570, and their stability was measured using the centrifugation method and Equation 1 described above.

Example 1

Stability of a Phytosterol Dispersion Prepared in Accordance to the Assay No. 5 of Example 1 of the US Patent Application 20040029844.

250 g of phytosterols, 25 g of sucrose stearyl ester (Sisterna SP50) and 17.5 g of sorbitan lauryl ester (Span 20) were melted together at 135° C. The melted mixture was added to 5000 g of water kept at 80° C. The mixture was stirred at 7000 rpm for 15 minutes. 100 g of the formed dispersion were removed and left to cool down to room temperature (Sample 1.1). Additionally, 500 g of the formed dispersion were fed to a homogenizer (APV-Gaulin, model MR-15) and homogenized in one stage at 480 bar. The homogenized mixture was subsequently left to cool down to room temperature (Sample 1.2).

The stability of both samples was determined according to Equation 1. The non-homogenized mixture (sample 1.1) yielded a stability of 28.2%. The homogenized mixture (sample 1.2) yielded a stability of 41.5%.

Both samples contained about 4.7% of phytosterols by weight of dispersion and had an emulsifier/phytosterol ratio of about 17.0%. Both emulsifier mixtures had an HLB value of about 10.

Example 2

Stability of a Phytosterol Dispersion Prepared in Accordance to Example 1 of the US Patent Application 20070031570.

500 g of water were heated in a vessel to 49° C. Then 33.3 g of soy lecithin were added and stirred during 20 minutes. Next, 16.7 g of phytosterols, and 50 g of maltodextrin were added to the vessel and the resulting mixture was further stirred for another 20 minutes. Subsequently, the mixture was heated to 74° C. and placed in a high-pressure 1-liter laboratory Parr reactor. The mixture was heated to 152° C. for 1.5 minutes by means of the addition of live steam through a valve located at the reactor head. Next, the reactor was quickly cooled down to a mixture temperature of 79° C. Upon opening the reactor, 200 g of the dispersion were taken and left to cool down to room temperature (Sample 2.1).

Additionally, 300 g of the dispersion at 79° C. were fed to a homogenizer (APV-Gaulin, model MR-15) and homogenized in two stages, at 240 and 35 bar respectively, and then were left to cool down to room temperature (Sample 2.2).

The stability of both samples was determined according to Equation 1. The non-homogenized mixture (sample 2.1) yielded a stability of 17.4%. The homogenized mixture (sample 2.2) yielded a stability of 31.5%.

Both samples contained in average about 3.3% of phytosterols by weight of dispersion and had an emulsifier/phytosterol ratio of about 199.0%. The HLB value for soy lecithin is about 3.8.

Example 3

Stability of Phytosterol Dispersions Prepared by the Process of the Present Invention Using the Emulsifiers of Examples 1 and 2.

Assay 3.1

A 1-liter Parr reactor (Parr Instrument Company, Moline, Ill. USA) provided with a turbine stirrer, nitrogen and vacuum lines and controlled electric heating was loaded with soft water, phytosterols and one or more emulsifiers according to Table 4. The closed reactor was evacuated during 2 minutes with stirring at 30 rpm. Then, the stirrer speed was increased to 700 rpm and the reactor content was heated to 160° C. during 10 minutes. Next, the reactor was left to cool down to 25° C. and the internal pressure was equalized to atmospheric pressure with nitrogen. A sample was withdrawn from the dispersion and its stability percentage was determined.

TABLE 4

| Assay | Phytosterols (g) | Sisterna SP50 (g) (sucrose stearyl ester) | Water (g) | Stability (%) |
|---|---|---|---|---|
| 3.1 | 25.0 | 2.5 | 500 | 85 |

Assay 3.2

The previous assay was repeated under the operation conditions of assay 3.1, but varying the amount of phytosterols and the amount and type of emulsifier as shown in Table 5.

TABLE 5

| Assay | Phytosterols (g) | Soy lecithin (g) | Water (g) | Stability (%) |
|---|---|---|---|---|
| 3.2 | 16.7 | 33.3 | 500 | 89 |

Two additional phytosterol emulsions were subsequently prepared according to the previous conditions and were homogenized at 160° C. After cooling the homogenized emulsions to room temperature, their stability was higher than 99%.

From the results of Example 3, it can be observed that the process of the invention, unlike the processes of the state of the art, allows the preparation of highly stable phytosterol dispersions without an homogenization step, both with a low-HLB value emulsifier (soy lecithin HLB 3.8) and a high-HLB value emulsifier (sucrose stearyl ester, HLB 11).

Example 4

Phytosterol Dispersions Prepared with Sodium Salts of Sunflower Fatty Acids (SSSFA).

Assay 4.1

A 1-liter Parr reactor (Parr Instrument Company, Moline, Ill. USA) provided with a turbine stirrer, nitrogen and vacuum lines and controlled electric heating was charged with 500 g of soft water, 5 g of phytosterols and 0.05 g of SSSFA. The closed reactor was evacuated during 2 minutes with stirring at 30 rpm. Then, the stirrer speed was increased to 700 rpm and the reactor content was heated to 160° C. during 10 minutes. Next, the reactor was left to cool down to 25° C. and the internal pressure was equalized to the atmospheric pressure with nitrogen. A sample was withdrawn from the dispersion and its stability was assessed to be higher than 99%, as shown in Table 6. The assay was repeated six more times (assays 4.2 to 4.7) under the same operation conditions but using different amounts of phytosterols and SSSFA each time, and the stability of the resulting dispersions was determined as shown in Table 6. In all cases, the stability of the resulting dispersions was higher than 99%.

TABLE 6

| Assay | Phytosterols (g) | SSSFA (g) | Water (g) | Stability (%) |
|---|---|---|---|---|
| 4.1 | 5 | 0.05 | 500 | >99 |
| 4.2 | 10 | 0.1 | 500 | >99 |
| 4.3 | 50 | 0.5 | 500 | >99 |
| 4.4 | 100 | 1.0 | 500 | >99 |
| 4.5 | 150 | 1.5 | 500 | >99 |
| 4.6 | 200 | 2.0 | 500 | >99 |
| 4.7 | 250 | 2.5 | 500 | >99 |

As can be assessed from the values set forth in Table 6, the dispersions had over 99% of stability with only 1% of SSSFA emulsifier relative to phytosterols.

When the overall phytosterol content of the dispersions was over 5%, the resulting dispersions had a higher viscosity, making them more suitable for food formulations such as dairy products, margarines, mayonnaises, and others, imparting good stability and superior palatability to such products.

Example 5

Phytosterol Dispersions Prepared with Sodium Salts of Coconut Oil Fatty Acids.

The assay 4.3 of Example 4 was replicated using 7.5 g of sodium salts of coconut oil fatty acids as emulsifier instead of 0.5 g sodium salts of sunflower oil fatty acids. The resulting dispersion was a semitransparent gel having a stability of 100%. The dispersion was readily incorporated into food items.

Example 6

Stability of Homogenized Dispersions
Assay 6.1

A 300-liter 316 stainless-steel reactor provided with a turbine stirrer and internal baffles, nitrogen and vacuum line, a heating jacket heated with thermal oil and a cooling jacket, was loaded with 150 kg of soft water, 1.5 kg of phytosterols and 150 g of Span 20. The closed reactor was evacuated to 50 mbar at a stirring speed of 15 rpm and then equalized with nitrogen. Next, the stirring speed was increased to 330 rpm and the content of the reactor was heated at 160° C. for 20 minutes.

The emulsion obtained at 160° C. was fed to a heated MR-15 APV-Gaulin homogenizer and was homogenized in two stages, at 300 and 50 bar respectively. A sample of the homogenized emulsion was withdrawn and let to cool down to room temperature. The stability of the resulting dispersion was 90%, as shown in Table 7. The described assay was replicated under the same operation conditions for several other combinations of type of emulsifier and phytosterols/emulsifier ratios as shown in Table 7.

TABLE 7

| Assay | Water (kg) | Phytosterols (kg) | Emulsifier (g) | Emulsifier type | Emulsifier HLB | Stability of the dispersion (%) |
|---|---|---|---|---|---|---|
| 6.1 | 150 | 1.5 | 150 | Span 20 | 8.6 | 90 |
| 6.2 | 150 | 1.5 | 150 | Monoglycerides | 3-4 | 94 |
| 6.4 | 150 | 1.5 | 150 | Sodium stearoyl lactylate | 8.3 | 94 |
| 6.5 | 150 | 1.5 | 150 | Sucrose ester | 16 | >99 |
| 6.8 | 150 | 3.0 | 30 | Sodium oleate | 20 | >99 |
| 6.9 | 150 | 1.5 | 30 | Sodium oleate | 20 | >99 |
| 6.10 | 150 | 1.5 | 150 | Monoglycerides | 3-4 | >99 |
| 6.11 | 150 | 1.5 | 15 | Sucrose ester | 16 | 91 |
| 6.12 | 150 | 1.5 | 55 | Sucrose ester | 16 | 96 |
| 6.13 | 150 | 1.5 | 15 | Sodium stearoyl lactylate | 8.3 | 90 |
| 6.14 | 150 | 1.5 | 15 | Monoglycerides | | 88 |
| 6.15 | 150 | 1.5 | 600 | Tween 20 | 15 | 89 |
| 6.16 | 150 | 1.5 | 600 | Sodium oleate | 20 | >99 |
| 6.17 | 150 | 1.5 | 300 | Sodium laurate | 20.4 | >99 |
| 6.18 | 150 | 3.0 | 300 | Sodium oleate | 20 | >99 |
| 6.19 | 150 | 15 | 300 | Sodium oleate | 20 | >99 |
| 6.20 | 150 | 50 | 2000 | Sodium oleate | 20 | >99 |
| 6.21 | 150 | 30 | 1500 | Sodium oleate | 20 | >99 |

As observed from the values in Table 7, the processes herein disclosed allow for the preparation of highly stable aqueous phytosterol dispersions using a wide array of emulsifiers ranging from low-HLB emulsifiers (monoglycerides) to high-HLB emulsifiers (sodium oleate), a broad range of phytosterol concentrations and a wide range of phytosterol/emulsifier ratios.

Example 7

Stability of Dispersions with a Mixture of Emulsifiers

A series of phytosterol dispersion were prepared as described in Example 4 using a mixture of potassium stearate and Tween 80 with different relative proportions as shown in Table 8 together with the respective stability of the resulting dispersion.

TABLE 8

| Assay | Phytosterols (g) | Potassium stearate/ Tween 80 (g/g) | Water (g) | Stability (%) |
|---|---|---|---|---|
| 7.1 | 5 | 0.25/0.25 | 500 | 87 |
| 7.2 | 10 | 0.5/0.5 | 500 | 89 |
| 7.3 | 50 | 0.5/2.5 | 500 | 92 |
| 7.4 | 100 | 1.0/5.0 | 500 | 91 |
| 7.5 | 150 | 3.0/15.0 | 500 | 91 |
| 7.6 | 200 | 4.0/15.0 | 500 | 95 |

As observed in Table 8, emulsifier mixtures can also be formulated to get highly stable dispersions. When substituting Tween 80 with polysorbates, highly stable dispersions were obtained again. These dispersions are readily incorporated into food matrixes such as beverages, dairy products, margarines, mayonnaises and others.

Example 8

Soybean Phytosterol Dispersions Prepared with Sodium Salts of Sunflower Fatty Acids (SSSFA).

Example 4 was replicated using soybean phytosterols with the composition shown in Table 9.

TABLE 9

Composition of soybean phytosterols.

| Phytosterol | % in weight |
|---|---|
| Campesterol | 25.6 |
| Campestanol | 0.9 |
| Stigmasterol | 16.3 |
| Sitosterol | 49.0 |
| Sitostanol | 1.4 |
| Other phytosterols | 6.5 |

The stability of the resulting dispersions was higher than 99%, as in the case of tall oil phytosterol dispersions prepared in the same manner.

Example 9

Phytostanol (Hydrogenated Phytosterol) Dispersions Prepared with Sodium Salts of Sunflower Fatty Acids (SSSFA).

A dispersion of phytostanols having the composition indicated in Table 10 was prepared according to the conditions of the Example 4, but with the Parr reactor operating at 173° C. instead of 160° C.

TABLE 10

Phytostanol composition in Example 9

| Phytostanol | % in weight |
|---|---|
| Campesterol | 0.1 |
| Campestanol | 31.4 |
| Stigmasterol | 0.0 |
| Sitosterol | 0.3 |
| Sitostanol | 64.9 |
| Other phytosterols | 1.2 |

The stability results in this case were similar to those obtained using tall oil phytosterols, i.e. a stability higher than 99%

Example 10

Stability of Phytosterol Dispersions Prepared with Skimmed Milk in a Continuous Process.

The experimental set up for this experiment consisted in a first plate heat exchanger (HE 1) o heat the aqueous feed to a first 1-liter Parr reactor (P1) provided with a turbine stirrer, a second plate heat exchanger (HE 2) provided with a discharge valve and operated at 5° C. to cool the phytosterol dispersion discharged from P1 and a second Parr reactor (P2) heated with an electric tape and connected to P1 through a gear pump, containing liquid phytosterols at 160° C. under a nitrogen atmosphere. HE 1 was heated with thermal oil at 170° C. and was connected to a feeding tank through a gear pump. The HE 1-P1-HE 2 system was first operated with soft water until, and a steady state of 20 seconds of residence time was reached by adjusting the flow when the temperature in P1 was 160° C. Then the feed was substituted by skimmed milk containing sodium salts of sunflower fatty acids at a concentration of 50 mg/liter.

After a few minutes, P1 was fed from P2 with liquid phytosterols at 160° C. at a rate of 20 g/minute and, after reaching a new steady state, samples of the phytosterol dispersion in skimmed milk were taken at the outlet of HE 2.

No phase separation was observed and the samples had a neutral flavor and good palatability. Samples had a stability of 99%.

Example 11

Stability of Phytosterol Dispersions Prepared with Soymilk in a Continuous Process.

Example 10 was replicated using soymilk instead of skimmed milk. A phytosterol dispersion in soymilk was obtained. No phase separation was observed, the samples had a neutral flavor and the presence of phytosterols was not palatable. The stability percentage of the samples was 99%.

Example 12

Stability of a Highly Concentrated Phytosterol Dispersion Prepared with Skimmed Milk in a Continuous Process.

The experimental set up of Example 10 was modified to carry out the Example 12 as follows: a third heat exchanger (HE 3) was inserted between P1 and HE 2. A third Parr reactor (P3) containing skimmed milk was connected to HE 3 through a gear pump. In this example, the temperature of the molten phytosterols in P2 (under a nitrogen atmosphere as in Example 10) was 165° C.

The HE 1-P1-HE 3-HE 2 system was first operated with a solution of 0.65% sodium oleate in soft water at a rate of 100 mL/min entering P1 through HE 1 at 165° C. and leaving HE 2 at 15° C. After some time, molten phytosterols from P2 began to be fed to P1 at a rate of 35 mL/min, and a viscous phytosterol dispersion at 63° C. was discharged through HE 2. Under this conditions, skimmed milk from P3 was fed to HE 3 at a rate of 7 L/min and the whole system was operated to reach a steady state. Samples were taken afterward. No phase separation was observed and the samples had a neutral flavor and good palatability. The samples had a stability of 99%.

Example 13

Preparation of a Dispersible Phytosterol Powder 100 kg of the phytosterol dispersion of assay 6.1 of Example 6 were loaded into a 500-liter mixer provided with a central paddle stirrer. 250 g of maltodextrin were added with stirring. The resulting mixture was then fed using a Moyno pump at a rate of 1.5 L/min to a Niro Atomizer provided with an atomizer disc rotating at 12,000 rpm. The inlet and outlet temperatures were 210° C. and 105° C., respectively. 745 g of powdered phytosterols were collected. The powder was readily resuspendable in water with no need of vigorous stirring or homogenization.

Example 14

Preparation of Dispersible Phytosterol Powders

The procedure of Example 13 was repeated with the phytosterol dispersions of assays 6.2, 6.5, 6.8, 6.10, 6.19, 6.20 and 6.21 of Example 6. The phytosterols powders obtained in each assay were readily resuspendable in water, milk, soymilk, herb infusions and coffee drink with under mild agitation.

Example 15

Unstable Phytosterol Dispersion

The procedure of Example 13 was repeated using 100 liters of a phytosterol dispersion prepared according to the procedure of Example 2. The resulting phytosterol powder settled down quickly upon resuspension in water.

Example 16

Assessment of the Effect of the Consumption of Phytosterol Dispersions and Dispersible Phytosterol Powders on the In Vivo Absorption of Dietary Cholesterol Twenty-six 21-day old C57/BL6 mice were freely fed with a commercial low-cholesterol base diet (<0.02% cholesterol; Prolab RMH3000; PMI Feeds, St. Louis, Mo.) and were divided into five groups. Each of these five groups were fed ad libitum access to an additional ingredient in their diet together with the basal diet, which for each group was as follows:

Control group (n=5): 0.01% aqueous solution of sodium oleate
Group 1 (n=5): phytosterol suspension of the assay 6.8 of Example 6
Group 2 (n=6): aqueous 1% by weight phytosterol suspension prepared using dispersible phytosterols prepared according to Example 14 from the corresponding assay 6.8
Group 3 (n=5): aqueous 2% by weight emulsion of phytostanol esters
Group 4 (n=5): 1% by weight phytosterol suspension prepared from the dispersible phytosterol powders prepared in Example 15.

The estimated daily consumption dose per mice was 100 mg of phytosterols or phytostanols.

For the determination of the cholesterol absorption, the method of dual isotopic ratio in feces was used as described by Schwarz et al. (Schwarz M, Russell D W, Dietschy J M, Turley S D. (1998) *Marked reduction in bile acid synthesis in cholesterol 7α-hydroxylase-deficient mice does not lead to diminished tissue cholesterol turnover or to hypercholesterolemia J. Lipid Res.* 39: 1833-1843), which consists in the indirect measurement of the difference between the radioactivity of a single dose of radiolabeled cholesterol administered by gavages and that found collected feces 24 h the administration of radiolabeled cholesterol. The method includes the joint administration of a non-absorbable radiolabeled internal sitostanol standard together with the radioactive cholesterol, for the calibration of measurements.

After 40 days of feeding each group with the aforementioned diets, the animals were given a single dose containing 1 uCi of [4-$^{14}$C]-cholesterol together with 2 uCi of [5,6-$^3$H]-sitostanol. Feces corresponding to a period of 24 hours were collected. Total lipids were extracted from the oral mixture dose and from feces, and the difference in the $^{14}$C/$^3$H ratio was calculated. Results are shown in Table 11.

TABLE 11

| Group | Cholesterol absorption (%) | Cholesterol absorption reduction (%) |
| --- | --- | --- |
| Control (n = 5) | 72 ± 4 | |
| Group 1 (n = 5) | 38 ± 4[a,b] | 47 |
| Group 2 (n = 6) | 44 ± 3[a,b] | 38 |
| Group 3 (n = 5) | 55 ± 3[a] | 24 |
| Group 4 (n = 5) | 62 ± 5 | 14 |

[a] $p < 0.05$, Mann-Whitney non-parametric U-test with respect to the Control group
[b] $p < 0.05$, Mann-Whitney non-parametric U-test with respect to Group 3

The results show that the average cholesterol absorption is 72%. The animals from Group 4 that were fed with the phytosterol suspension prepared from the dispersible phytosterol powders of Example 15, experienced the lower reduction in cholesterol absorption, only 14% of reduction with respect to the Control group. These were followed by the animals from Group 3, whose diet included aqueous dispersions of phytostanol esters, which have been scientifically well acknowledged for their action. Group 1 showed the higher cholesterol absorption reducing capacity, around 47% with respect to the Control group, thus evidencing that the dispersions prepared according to the methods of the present invention are highly efficient to reduce cholesterol absorption. Likewise, the dispersible phytosterol powders prepared according to the processes of the present invention (Group 2) are significantly better to reduce cholesterol absorption than dispersible powders of phytostanol esters and phytosterols prepared according to other processes disclosed in the state of the art.

Example 17

Salad Dressing

A salad dressing containing free dispersed phytosterols was prepared with the formula shown in Table 12:

TABLE 12

| Ingredient | % in weight |
| --- | --- |
| Canola oil | 14.0 |
| Vinegar | 5.8 |
| Dispersion of the assay 4.3 of Example 4 | 70.2 |
| Salt | 1.5 |
| Sugar | 3.7 |
| Spices and flavoring agents | 3.5 |
| Carboxymethylcellulose | 1.2 |

The phytosterol dispersion, salt, sugar, spices and flavoring agents were mixed in a stirred vessel, then the other ingredients were slowly added with constant stirring and the mixture was homogenized. Finally, species and flavoring agents were added with stirring. The salad dressing prepared according to this procedure had desirable consistence and taste characteristics.

Example 18

Preparation of a Dairy Drink

A dairy drink containing dispersed phytosterols was prepared according to the formula presented in Table 13:

TABLE 13

| Ingredient | % in weight |
| --- | --- |
| Powdered milk | 15 |
| Dispersion of the assay 6.5 of Example 6 | 85 |

The dispersion of phytosterols was heated to 40° C. and then mixed with the powdered milk in a stirred vessel. The resulting mixture was pasteurized at 84° C. and quickly cooled down to 5° C.

Example 19

Preparation of a Margarine

A margarine containing dispersed phytosterols was prepared according to the formula presented in Table 14:

TABLE 14

| Ingredient | % in weight |
| --- | --- |
| Vegetable oil | 43 |
| Dispersion of the assay 4.4 of Example 4 | 50 |
| Fat | 2 |
| Butter | 3 |
| Salt | 1.4 |
| Mono- and diglycerides | 0.4 |
| Flavor | 0.07 |
| Lecithin | 0.08 |
| Potassium sorbate | 0.05 |

The dispersion of phytosterols was heated to 80° C. and mixed with the salt, mono- and diglycerides, water-soluble flavors and potassium sorbate with constant stirring. The resulting homogeneous mixture was pasteurized at 60° C. The vegetable oil was heated to 80° C., mixed with the fat, butter, oil-soluble flavors and lecithin to form a homogeneous mixture. Then, the aqueous mixture was added with stirring at 70° C. to form an emulsion. The emulsion was subsequently cooled down and packed.

Example 20

Preparation of a Yoghurt

A yoghurt containing dispersed phytosterols was prepared according to the formula presented in Table 15:

TABLE 15

| Ingredient | % in weight |
| --- | --- |
| Dispersion of the assay 6.10 of Example 6 | 75 |
| Powdered milk | 17 |
| Sugar | 6 |
| Stabilizers | 2 |

The dispersion of phytosterols was heated to 40° C. and mixed with the powdered milk. The mixture was pasteurized and then the sugar was incorporated into the pasteurized mixture. Lactic yoghurt cultures were added to the mixture, which was subsequently incubated at 37° C. until reaching pH 4.2. A mixture of stabilizers was then added and the resulting yoghurt was packed.

What is claimed is:

1. A process for the production of an aqueous dispersion of one or more phytosterols comprising the steps of:
    a) adding each of the following components to a heated disperser in a single step: one or more phytosterols, 5 mg to less than 10 mg of one or more sodium or potassium salt of an organic acid per gram of phytosterols, the organic acid having from 10 to 24 carbon atoms, and water; and then dispersing the mixture at a temperature in the range of 150° C. to 200° C. to produce an aqueous emulsion of phytosterol or phytosterols; and
    b) cooling the emulsion to produce an aqueous dispersion of phytosterol or phytosterols; provided that the sodium or potassium salt of an organic acid having from 10 to 24 carbon atoms is not sodium stearoyl lactylate.

2. The process according to claim 1, wherein the disperser is a stirred vessel.

3. The process according to claim 2, wherein the organic acid is a fatty acid.

4. The process according to claim 2, wherein in step a) 0.05 g of a mixture of sodium salts of sunflower fatty acids and 5 g of phytosterols are dispersed in water at 160° C.

5. The process according to claim 1, wherein the organic acid is a fatty acid.

6. The process according to claim 1, wherein in step a) 0.05 g of a mixture of sodium salts of sunflower fatty acids and 5 g of phytosterols are dispersed in water at 160° C.

7. A process for the production of an aqueous dispersion of one or more phytosterols comprising the steps of:
    a) adding each of the following components to a heated disperser in a single step: one or more phytosterols, 5 mg to less than 10 mg of one or more sodium or potassium salt of an organic acid per gram of phytosterols, the organic acid having from 10 to 24 carbon atoms, and water; and then dispersing the mixture at a temperature in the range of 150° C. to 200° C. to produce an aqueous emulsion of phytosterol or phytosterols;
    b) homogenizing the emulsion in a pressurized homogenizer; and
    c) cooling the homogenized emulsion to produce an aqueous dispersion of phytosterol or phytosterols; provided that the sodium or potassium salt of an organic acid having from 10 to 24 carbon atoms is not sodium stearoyl lactylate.

8. The process of claim 7, wherein the organic acid is a fatty acid.

9. The process of claim 8, wherein the fatty acid is oleic acid.

* * * * *